United States Patent [19]

Inoue et al.

[11] Patent Number: 4,676,925
[45] Date of Patent: Jun. 30, 1987

[54] LIQUID CRYSTALLINE BIPHENYL DERIVATIVES AND MIXTURES THEREOF

[75] Inventors: Hiromichi Inoue; Shinichi Saito; Kanetsugu Terashima; Takashi Inukai, all of Yokohama; Kenji Furukawa, Yokosuka, all of Japan

[73] Assignee: Chisso Corporation, Osaka, Japan

[21] Appl. No.: 853,851

[22] Filed: Apr. 21, 1986

Related U.S. Application Data

[62] Division of Ser. No. 613,974, May 24, 1984, Pat. No. 4,614,609.

[30] Foreign Application Priority Data

Jun. 14, 1983 [JP] Japan ........................ 58-106100
Jul. 5, 1983 [JP] Japan ........................ 58-121769

[51] Int. Cl.⁴ ............... C09K 19/12; C07C 69/76
[52] U.S. Cl. ................ 252/299.65; 560/73; 560/108; 350/350 S; 252/299.01
[58] Field of Search ........ 252/299.65, 299.67, 252/299.66, 299.01; 350/350 S; 560/73, 107, 108

[56] References Cited

U.S. PATENT DOCUMENTS

| | | | |
|---|---|---|---|
| 4,065,489 | 12/1977 | Steinstrasser et al. | 252/299.65 |
| 4,136,053 | 1/1979 | Steinstrasser et al. | 252/299.65 |
| 4,149,413 | 4/1979 | Gray et al. | 350/350 R |
| 4,195,916 | 4/1980 | Coates et al. | 350/350 R |
| 4,257,911 | 3/1981 | Gray et al. | 350/350 S |
| 4,264,148 | 4/1981 | Gobl-Wunsch et al. | 350/346 |
| 4,576,732 | 3/1986 | Isogai et al. | 252/299.67 |
| 4,589,996 | 5/1986 | Inoue et al. | 350/350 R |
| 4,592,858 | 6/1986 | Higuchi et al. | 252/299.66 |
| 4,596,667 | 6/1986 | Inukai et al. | 252/299.65 |
| 4,613,209 | 9/1986 | Goodby et al. | 350/350 S |

FOREIGN PATENT DOCUMENTS

| | | | |
|---|---|---|---|
| 115693 | 8/1984 | European Pat. Off. | 252/299.65 |
| 59-128357 | 7/1984 | Japan | 252/299.65 |
| 59-219251 | 12/1984 | Japan | 252/299.65 |

OTHER PUBLICATIONS

Goodby et al., Liq. Cryst. Ord. Fluids, vol. 4, 1984, pp. 1-32, from Proceeding of ACS Symposium in USA, 1982.

Gray et al., Mol. Cryst. Liq. Cryst., vol. 37, 1976, pp. 157-188.

*Primary Examiner*—Teddy S. Gron
*Assistant Examiner*—J. E. Thomas
*Attorney, Agent, or Firm*—Fred Philpitt

[57] ABSTRACT

Chiral smectic compounds having a high response rate and being superior as a ferroelectric liquid crystalline material, and chiral smectic mixtures containing the same are provided, which compounds being expressed by the formula

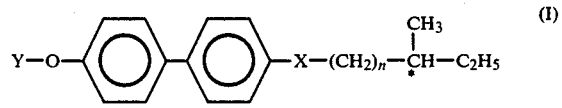

wherein X represents $-CH_2-$, $-O-$ or $-CO-$; n represents 0, 1 or 2; when X represents $-CH_2-$, Y represents $R-$, $R-CO-$, $ROCO-$,

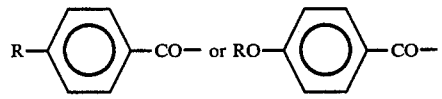

wherein R represents an alkyl group having 1 to 18 carbon atoms, and when X represents $-O-$ or $-CO-$, Y represents R; and * represents a symbol indicating an optically active carbon atom.

6 Claims, No Drawings

LIQUID CRYSTALLINE BIPHENYL DERIVATIVES AND MIXTURES THEREOF

This is a division of application Ser. No. 613,974, filed May 24, 1984, now U.S. Pat. No. 4,614,609, and the benefits of 35 USC 120 are claimed relative to it.

BACKGROUND OF THE INVENTION

1. Field of the Invention

This invention relates to novel liquid crystalline compounds and liquid crystalline mixtures containing the same, and more particularly, it relates to chiral smectic compounds which have a high response rate and are superior as a ferroelectric liquid crystalline material, and also to chiral smectic mixtures containing the same.

2. Description of the Prior Art

Twisted nematic (TN) type display mode has currently been most widely employed as liquid crystal display elements, but it is inferior in the response rate as compared with emissive type display elements such as electroluminescence, plasma display, etc., and various attempts for overcoming this drawback have been made, but, nevertheless, it seems that its improvement to a large extent has not been left behind. Thus, various liquid crystal display equipments based on different principles in place of TN type display elements have been attempted, and as one of them, there is a display mode utilizing ferroelectric liquid crystals (N. A. Clark and S. T. Layerwall, Applied Phys. lett., 36,899 (1980)). This mode utilizes the chiral smectic C phase (hereinafter abbreviated to SC* phase) or chiral smectic H phase (hereinafter abbreviated to SH* phase) of ferroelectric liquid crystals. As such ferroelectric liquid crystal compounds, the following compounds (1) to (4) have been known up to the present (ph. Martino Lagarde, J. de Physique, 37, C3-129 (1976)):

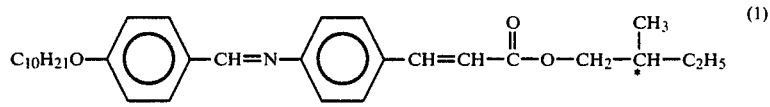
(1)

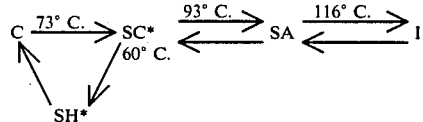

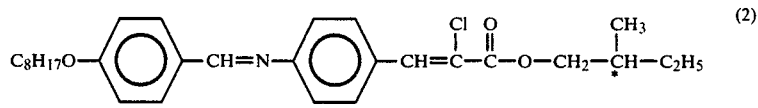
(2)

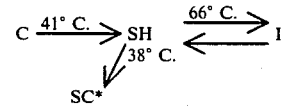

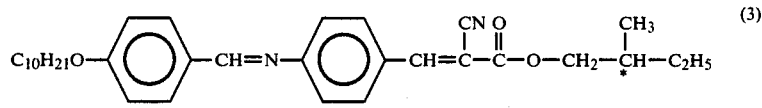
(3)

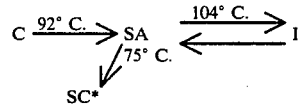

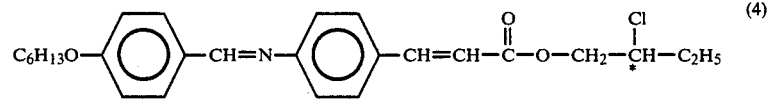
(4)

In the foregoing, C represents crystalline phase; SA, smectic A phase; I, isotropic liquid phase; SC* and SH*, as described above; and "*", asymmetric carbon atom.

Further, as ferroelectric liquid crystal compounds, the following two compounds (5) and (6) have also been known:

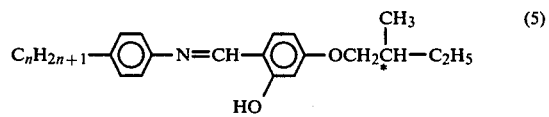
(5)

(n = 7, 8, 9, 10)

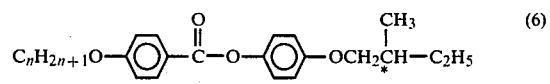
(6)

(n = 9, 10)

(B. I. Ostrovski, A. Z. Rabinovich, A. S. Sonin, E. L. Sorkin, B. A. Strukov, and S. T. Taraskin; Ferroelectrics, 24, 309 (1980)).

Among these compounds, since the compounds (1) to (4) have C=C double bond and azomethine group, they have drawbacks of being inferior in light resistance and water resistance. The compounds (5) also have azomethine group and hence are inferior in water resistance. The compounds (6) do not have these bonds and hence are superior in stability, but the above Ostrovski et al's article discloses as to their phase transition temperatures, only that the upper limit temperatures of SC* phase are 324.8° K. (in the case of n=9) and 326.2° K. (in the case of n=10), but nothing is disclosed therein as to other liquid crystalline phase modifications.

The present inventors have investigated and studied various compounds including the above compounds (1) to (6) and as a result, have found ferroelectric liquid crystal compounds having a superior stability.

A group of these compounds is those previsouly filed as U.S. Ser. No. 568,060 (Jan. 4, 1984) now U.S. Pat. No. 4,596,667, and expressed by the following general formula:

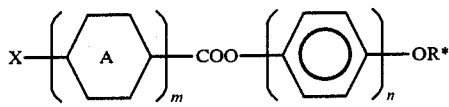
(7)

wherein

represents 1,4-phenylene group

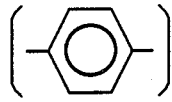

or 1,4-trans-cyclohexane group

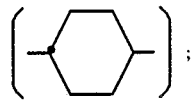;

R*, an optically active alkyl group; m=0, 1 or 2; n=1 or 2; X, a linear chain or brached alkyl group or alkoxy group, each having 1 to 18 carbon atoms; and when

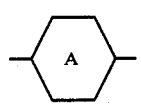

represents

m=1; and n=1, X represents a linear chain or branched alkyl group having 1 to 18 carbon atoms or a linear chain alkoxy group having 11 to 18 carbon atoms.

The compounds of the present invention are also used for the same object as that of the above compounds.

SUMMARY OF THE INVENTION

The present invention resides in:
Liquid crystalline compounds expressed by the formula

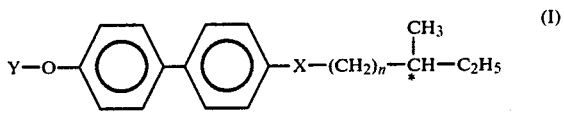
(I)

wherein X represents $-CH_2-$, $-O-$ or $-CO-$; n represents 0, 1 or 2; when X represents $-CH_2-$, Y represents $R-$, $R-CO-$, $ROCO-$,

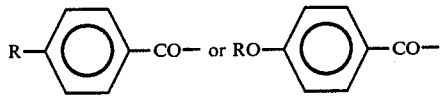

wherein R represents an alkyl group having 1 to 18 carbon atoms, and when X represents $-O-$ or $-CO-$, Y represents R; and * represents a symbol indicating an optically active carbon atom, and chiral smectic liquid crystalline compositions containing at least one kind of the same.

DESCRIPTION OF THE PREFERRED EMBODIMENTS

The compounds of the above formula (I) include those exhibiting SC* phase and Ch phase (cholesteric phase), those exhibiting SG phase (smectic G phase), SC* phase and Ch phase, those exhibiting more complicated multi-phases like Ch, SC*, SH* together with yet unidentified smectic modifications; that is, they are a group of compounds exhibiting physically very diversified crystalline phases.

Compounds of the general formula (I) wherein X represents $-CH_2-$ and Y represents RCO—, ROCO—,

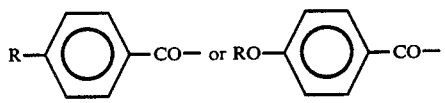

are expressed by the following general formula (II):

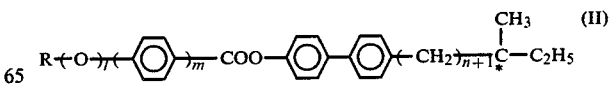
(II)

wherein l and m each represents 0 or 1; n represents 0, 1 or 2; and R is as defined above.

Most of the compounds of the formula (II) exhibit SC* phase within a broad temperature range and yet up to relatively high temperatures; hence when they are mixed with other compounds, it is possible to extend the upper limit of SC* temperature range of liquid crystalline compositions. Further, from most of the compounds of the formula (II), it is possible to easily obtain liquid crystalline compounds having cholesteric phase on the higher temperature side of smectic phase and exhibiting SC* phase in the vicinity of room temperature.

The following Table 1 shows concrete examples of the compounds of the formula (II) and their liquid crystalline phase transition points.

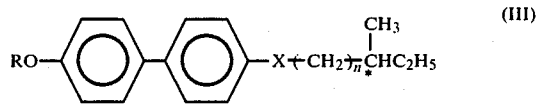

wherein R, n and X are as defined above.

As to the compounds of the formula (III), a number of the compounds exhibit a smectic phase and most of the compounds exhibit any or at least either one of SA phase, SH* phase and SC* phase. Among them, compounds exhibiting SH* phase and SC* phase are suitable as compounds used in a display mode utilizing ferroelectric properties, and when they are mixed with com-

TABLE 1

| Example | In formula (II) R | l | m | n | C | SG | SB | SC* | Ch | I |
|---|---|---|---|---|---|---|---|---|---|---|
| 2 | $C_3H_7$ | 0 | 1 | 1 | • 107.6 | — | — | — | • 148.6 | • |
| 3 | $C_4H_9$ | 0 | 1 | 1 | • 103.8 | — | — | — | • 138.5 | • |
| 4 | $C_5H_{11}$ | 0 | 1 | 1 | • 102.8 | — | — | (• 88.7) | • 143.6 | • |
| 5 | $C_7H_{15}$ | 0 | 1 | 1 | • 92.0 | — | — | • 97.8 | • 137.0 | • |
| 6 | $C_8H_{17}$ | 0 | 1 | 1 | • 84.9 | — | — | • 101.1 | • 131.6 | • |
| 7 | $C_9H_{19}$ | 0 | 1 | 1 | • 70.9 | — | — | • 103.3 | • 130.2 | • |
| 8 | $C_{10}H_{21}$ | 0 | 1 | 1 | • 50.9 | — | — | • 102.4 | • 121.9 | • |
| 9 | $C_3H_7$ | 1 | 1 | 1 | • 111.9 | — | — | — | • 174.6 | • |
| 10 | $C_4H_9$ | 1 | 1 | 1 | • 102.4 | — | — | (• 90.4) | • 176.3 | • |
| 11 | $C_5H_{11}$ | 1 | 1 | 1 | • 108.0 | — | — | (• 101.9) | • 167.0 | • |
| 12 | $C_6H_{13}$ | 1 | 1 | 1 | • 102.0 | — | — | • 112.2 | • 167.1 | • |
| 13 | $C_7H_{15}$ | 1 | 1 | 1 | • 97.1 | — | — | • 120.0 | • 161.6 | • |
| 1 | $C_8H_{17}$ | 1 | 1 | 1 | • 75.3 | — | — | • 126.8 | • 160.6 | • |
| 14 | $C_9H_{19}$ | 1 | 1 | 1 | • 80.2 | — | — | • 129.5 | • 154.9 | • |
| 15 | $C_{10}H_{21}$ | 1 | 1 | 1 | • 69.4 | • 76.6 | — | • 124.8 | • 148.0 | • |
| 16 | $C_{11}H_{23}$ | 1 | 1 | 1 | • 66.4 | • 82.2 | — | • 134.3 | • 150.3 | • |
| 17 | $C_{12}H_{25}$ | 1 | 1 | 1 | • 62.5 | • 79.3 | — | • 122.6 | • 124.9 | • |
| 18 | $C_{13}H_{27}$ | 1 | 1 | 1 | • 64.1 | • 83.7 | — | • 134.9 | • 147.6 | • |
| 19 | $C_7H_{15}$ | 0 | 0 | 1 | • 30.0 | — | • 66.0 | — | — | • |
| 20 | $C_8H_{17}$ | 1 | 0 | 1 | • 36.8 | — | — | (• 24.5) | (• 27.0) | • |
| 21 | $CH_3$<br>\|<br>$C_2H_5CHCH_2$ | 0 | 1 | 1 | • 102.4 | — | — | — | • 111.6 | • |
| 22 | $CH_3$<br>\|<br>$C_2H_5CHCH_2$ | 1 | 1 | 1 | • 98.5 | — | — | — | • 127.9 | • |

In Table 1, C represents a crystalline phase; SB, a smectic B phase; Ch, a cholesteric phase; and I, an isotropic liquid phase (transparent phase). The symbol • and the numeral on the right side thereof in the columns of the respective phases of the Table indicate a phase transition point from a phase to that on the right side thereof. The parenthese ( ) indicate a monotropic phase transition temperature.

Next, compounds of the formula I wherein Y=R are represented by the following general formula (III):

pounds exhibiting other SC* phase, SH* phase or cholesteric phase, they can serve to extend the temperature ranges of the SH* phase and SC* phase. Further, even in the case of compounds of the formula (III) which do not exhibit any smectic phase, it is possible for them to exhibit a similar effectiveness although its extent is inferior to that of the compounds exhibiting a smectic Phase.

The following Table 2 shows concrete examples of the compounds of the formula (III) and their liquid crystalline phase transition temperatures:

TABLE 2

| Example | In Formula (III) R | X | n | C | $S_2$ | $S_1$ | SH* | SC* | SA | I | Formula |
|---|---|---|---|---|---|---|---|---|---|---|---|
| 26 | $C_6H_{13}$ | O | 1 | •95.5 | — | — | — | — | — | • | (IIIc1) |
| 25 | $C_8H_{17}$ | O | 1 | •70.2 | — | •83.7 | •86.0 | — | — | • | |
| 27 | $C_{10}H_{21}$ | O | 1 | •76.0 | — | — | •78.3 | •80.3 | — | • | |
| 28 | $C_{12}H_{25}$ | O | 1 | •75.3 | — | (•73.9) | •77.4 | •78.9 | •79.8 | • | |
| 29 | $C_{14}H_{29}$ | O | 1 | •77.3 | — | — | — | — | — | • | |
| 30 | $C_{16}H_{33}$ | O | 1 | •78.9 | — | — | — | — | — | • | |
| 23 | $C_8H_{17}$ | CO | 1 | •70.4 | — | — | — | (•68.3) | •98.3 | • | (IIIa1) |
| 31 | $C_7H_{15}$ | $CH_2$ | 1 | •14.1 | •54.0 | •64.9 | — | — | — | • | (IIIb1) |
| 24 | $C_8H_{17}$ | $CH_2$ | 1 | •43.0 | — | •57.9 | •62.5 | •65.1 | — | • | |
| 32 | $C_9H_{19}$ | $CH_2$ | 1 | •58.4 | — | (•49.9) | •59.0 | •62.7 | •63.5 | • | |

TABLE 2-continued

| Exam-ple | In Formula (III) R | X | n | Phase transition point (°C.) C | S₂ | S₁ | SH* | SC* | SA | I | Formula |
|---|---|---|---|---|---|---|---|---|---|---|---|
| 33 | C₁₀H₂₁ | CH₂ | 1 | •47.3 | — | •51.0 | •53.6 | •58.9 | •62.9 | • | |

In the above Table, $S_1$ and $S_2$ each indicate an unidentified smectic phase, and others are the same as in Table 1.

When SC* liquid crystalline compositions are formed, it is possible to form them from a plurality of compounds of the formula (I), alone, and it is also possible to prepare liquid crystalline compositions exhibiting SC* phase, by mixing compounds of the formula (I) with other smectic liquid crystals.

When the light switching effect of the SC* phase is applied to display elements, the resulting display elements have the following three superior specific features:

The first specific feature is that the elements reply at a very high rate and the response times are 1/100 or less of those of display elements according to the usual TN display mode.

The second specific feature is that the elements have a memory effect; hence multiplex drive is easy in combination of this effect with the above-mentioned high rate response properties.

The third specific feature is that gray scale in TN display mode is attained by controlling the impressed voltage applied to display elements, but this is accompanied with difficult problems of the temperature depency of threshold voltage value and the voltage dependency of response rate. However, in the case where the light switching effect of SC* phase is applied to the display elements, it is possible to easily attain the gray scale by controlling the switching time of polarity; hence the display elements are very suitable for graphic display.

As for the display modes, the following two may be considered:

one mode is of birefringence type using two pieces of polarizers and another is of guest-host type using dichroic dyestuffs. Since SC* phase has a spontaneous polarization, molecules reverse around the helical axis thereof as a revolving axis by reversing the polarity of impressed voltage. A liquid crystal composition having SC* phase is filled into a liquid crystal display cell subjected to an aligning treatment so that liquid crystal molecules can align in parallel to the surface of electrodes, followed by placing the liquid crystal cell between two pieces of polarizers arranged so that the director of the liquid crystal molecules can be in parallel to the polarization plane on another side, impressing a voltage and reversing the polarity to be thereby able to obtain a bright field and a dark field (determined by the opposed angles of polarizers). On the other hand, in the case where display elements are operated in guest-host mode, it is possible to obtain bright field and colored field (determined by the arrangement of polarization sheets) by reversing the polarity of impressed voltage.

In general, it is difficult to align liquid crystal molecules in smectic state in parallel to the wall surface of glass; hence liquid crystal molecules have been aligned by cooling them very slowly (e.g. 1~2° C./hr) initially starting from their isotropic liquid, in a magnetic field of several tens Kilogauss or more, but in the case of liquid crystal substances having cholesteric phase, the substances are cooled at a cooling rate of 1° C./min. under impression of a direct current voltage of 50 to 100 V in place of magnetic field, whereby it is possible to easily obtain a monodomain state where liquid crystal molecules are uniformly aligned.

Compounds of the formula (I) also have an optically active carbon atom; hence when they are added to nematic liquid crystals, they have a performance of having a twisted structure induced in the mixtures. Nematic liquid crystals having a twisted structure, i.e. chiral nematic liquid crystals, form no reverse domain (striped pattern); hence it is possible to use the compounds of the formula (I) as an agent for preventing reverse domain. Compounds suitable for such an application field are those which by themselves exhibit cholesteric phase, and examples thereof are compounds of the formula (II) above.

When these compounds are added to nematic liquid crystals in an amount of about 0.05 to 3% by weight based on the latter, a twisting force in a definite direction is imparted to molecules so that the resulting nematic liquid crystals are free from the reverse domain.

In addition, racemi-form compounds corresponding to the compounds of the formula (I) are also liquid crystals exhibiting nearly the same phase transition points as those of the optically active form compounds of the formula (I), but they exhibit SH phase in place of SH* phase and SC phase in place of SC* phase, and when added to the optically active form compounds of the formula (I), they can be used for adjusting the chiral smectic pitch thereof. These racemi-form compounds can be prepared in the same manner as in the case of the optically active form compounds as mentioned later, if racemi-form raw materials are used therefor.

The preparation of the compounds of the formula (I) will be described for convenience in a divided manner by way of that of the compounds of the formula (II) and that of the compounds of the formula (III).

A. Preparation of compounds of the formula (II)

First, the compounds of the formula II wherein n=1 (hereinafter abbreviated to (IIa)) can be prepared by way of the following steps:

Chart 1

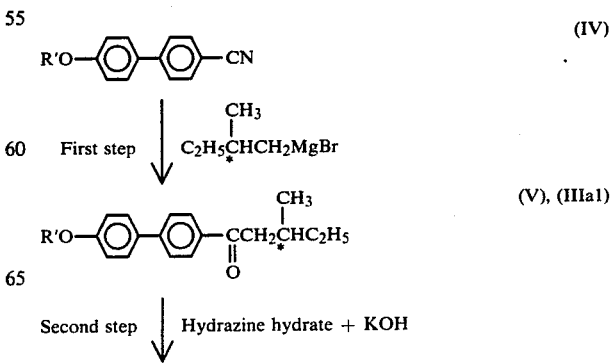

Chart 1 -continued

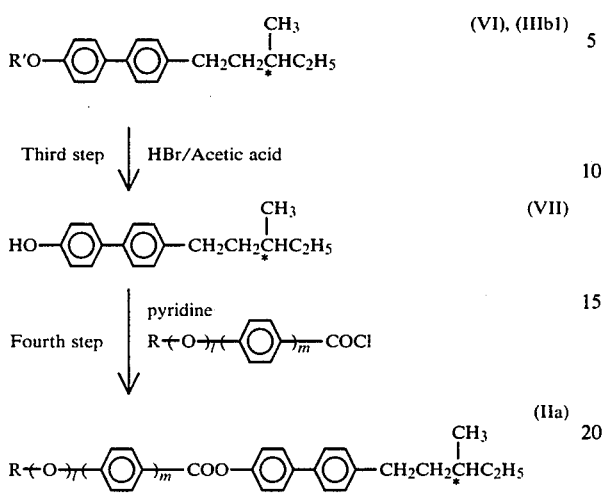

wherein R' represents a linear chain or branched alkyl of 1 to 10 carbon atoms and has no direct relation with R.

Namely, from (+) brominated 2-methylbutyl (prepared from (−)-2-methyl-1-butanol and phosphorus bromide) and metal Mg is prepared a Gringard reagent, which is then reacted with a p-alkyloxycyanobiphenyl (IV) as a commercially available product to obtain a compound of (V), which is then subjected to Wolff-Kishner reduction with hydrazine hydrate and potassium hydroxide to obtain a compound of (VI), which is then reacted with hydrobromic acid in acetic acid solvent to obtain a compound of (VII), which is then reacted in the presence of pyridine with a p-alkyloxybenzoic acid chloride, a p-alkylbenzoic acid chloride, an alkyl chloroformate or an aliphatic acid chloride correspondingly to l and m of the formula (II) to obtain the objective compounds of the formula (IIa). These compounds of the formula (IIa) prepared according to the above process are those wherein l=m=0 and R=from methyl to octadecyl, i.e. from 4-acetoxy-4'-(3-methyl-pentyl)biphenyl to 4-nonadecanoyloxy-4'-(3-methyl-pentyl)biphenyl; those wherein l=0, m=1 and R=from methyl to octadecyl, i.e. from 4-p-toluyloxy-4'-(3-methyl-pentyl)biphenyl to 4-p-octadecylbenzoyloxy-4'-(3-methyl-pentyl)biphenyl; those wherein l=1, m=0 and R=from methyl to octadecyl, i.e. from 4-methoxycarbonyloxy-4'-(3-methylpentyl)biphenyl to 4-octadecyloxycarbonyloxy-4'-(3-methyl-pentyl)biphenyl; and those wherein l=m=1 and R=from methyl to octadecyl, i.e. from 4-p-anisoyloxy-4'-(3-methyl-pentyl)biphenyl to 4-p-octadecyloxybenzoyloxy-4'-(3-methyl-pentyl)biphenyl.

In addition, compounds of (V) and compounds of (VI) which are intermediate compounds during the preparation steps of (IIa) are compounds of (III) wherein n=1 and X=—CH2— or —CO—, i.e. compounds of (IIIa1) and compounds of (IIIb1) described later.

Next, compounds of the formula (II) wherein n=0 (hereinafter abbreviated to (IIb)) can be prepared according to the following step:

Chart 2

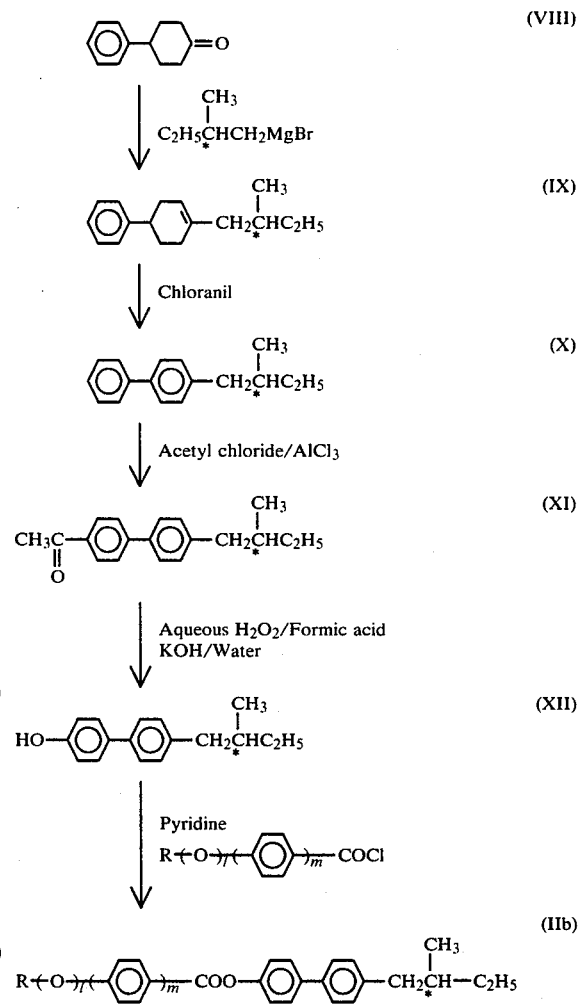

Namely, from (+) 2-methylbutylbromide and metal Mg is prepared a Gringard reagent, which is reacted with a known compound, 4-phenylcyclohexanone (VIII) to obtain a compound of (IX), which is heated with a dehydrogenating agent such as chloranil in a solvent to obtain a compound of (X), which is then subjected to Friedel-Krafts reaction with anhydrous aluminum chloride, acetyl chloride or the like in a solvent to obtain a compound of (XI), which is then reacted with formic acid and aqueous H2O2 to subject it to Bayer-Villiger reaction to thereby obtain an ester, which is hydrolyzed with water and potassium hydroxide to obtain a compound of (XII), which is then reacted in the presence of pyridine with a p-alkyloxybenzoic acid chloride, a p-alkylbenzoic acid chloride, an alkyl chloroformate or an aliphatic acid chloride correspondingly to l and m of the formula (II) to obtain the objective compounds of the formula (IIb). The compounds of the formula (IIb) thus prepared are those wherein l=m=0 and R=from methyl to octadecyl, i.e. from 4-acetoxy-4'-(2-methyl-butyl)biphenyl to 4-nonadecanoyloxy-4'-(2-methyl-butyl)biphenyl; those wherein l=0, m=1 and R=from methyl to octadecyl, i.e. from 4-p-toluyloxy-4'-(2-methyl-butyl)biphenyl to 4-p-octadecylbenzoyloxy-4'-(2-methyl-butyl)biphenyl;

those wherein l=1, m=0 and R=from methyl to octadecyl, i.e. from 4-methoxycarbonyloxyloxy-4'-(2-methyl-butyl)biphenyl to 4-octadecyloxycarbonyloxy-4'-(2-methyl-butyl)biphenyl; and those wherein l=m=1 and R=from methyl to octadecyl, i.e. from 4-p-anisoyloxy-4'-(2-methyl-pentyl)biphenyl to 4-p-octadecyloxybenzoyloxy-4-(2-methyl-butyl)biphenyl.

Next, compounds of the formula (II) wherein n=2 (hereinafter abbreviated to (IIc)) can prepared according to the following steps:

Chart 3

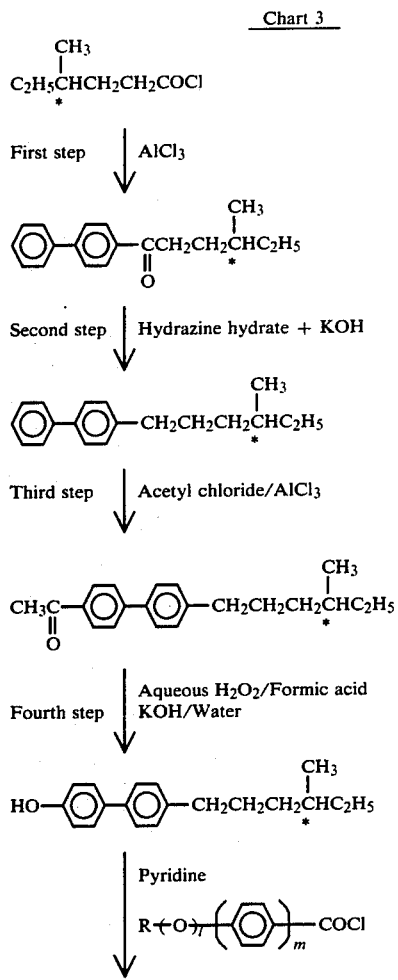

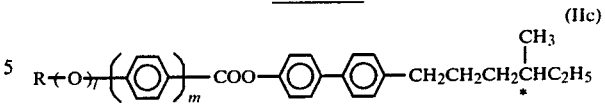

Namely, (+)-4-methylhexanoic acid (prepared according to the method of K. Vogler et al, Helv. Chim. Acta, 43, 279 (1960)) is reacted with thionyl chloride or the like to obtain an acid chloride (XIII), which is reacted with a commercially available product, biphenyl in a solvent to subject it to Friedel-Krafts reaction to thereby obtain a compound of (XIV), which is then subjected to Wolff-Kishner reduction with hydrazine hydrate and potassium hydroxide to obtain a compound of (XV), which is then subjected to Friedel-Krafts reaction with anhydrous aluminum chloride, acetyl chloride or the like in a solvent to obtain a compound of (XVI), which is then reacted with formic acid and aqueous H$_2$O$_2$ to subject it to Bayer-Villiger reaction to thereby obtain an ester, which is hydrolyzed with water and potassium hydroxide to obtain a compound of (XVII), which is reacted in the presence of pyridine with a p-alkyloxybenzoic acid chloride, a p-alkylbenzoic acid chloride, an alkyl chloroformate or an aliphatic acid chloride correspondingly to l and m of the formula (II) to obtain the objective compounds of the formula (IIc). Compounds of the formula (IIc) thus prepared are those wherein l=m=0 and R=from methyl to octadecyl, i.e. from 4-acetoxy-4'-(4-methyl-hexyl)biphenyl to 4-nonadecanoyloxy-4'-(4-methyl-hexyl)biphenyl; those wherein l=0, m=0 and R=from methyl to octadecyl, i.e. from 4-p-toluyloxy-4'-(4-methyl-hexyl)biphenyl to 4-p-octadecylbenzoyloxy-4'-(4-methyl-hexyl)biphenyl; those wherein l=1, m=0 and R=from methyl to octadecyl, i.e. from 4-methoxycarbonyloxy-4'-(4-methyl-hexyl)biphenyl to 4-octadecyloxycarbonyloxy-4'-(4-methyl-hexyl)biphenyl; and those wherein l=m=1 and R=from methyl to octadecyl, i.e. from 4-p-anisoyloxy-4'-(4-methyl-hexyl)biphenyl to 4-p-octadecyloxybenzoyloxy-4-(4-methyl-hexyl)biphenyl.

B. Preparation of compounds of the formula (III)

Compounds of the formula (III) wherein X=—CO—, and n=1 (IIIa1) are intermediate compounds of the formula (V) as previously referred to in the preparation of the compounds of the formula (IIa). Further, compounds of the formula (III) wherein X=—CO— and n=b 0 (IIIa0) and compounds of the formula (III) wherein X=—CO— and n=2 (IIIa2) are prepared through the processes shown in the following Chart 4:

Chart 4

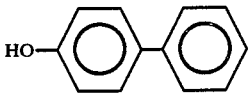

(XVIII)

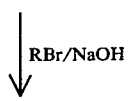

Chart 4

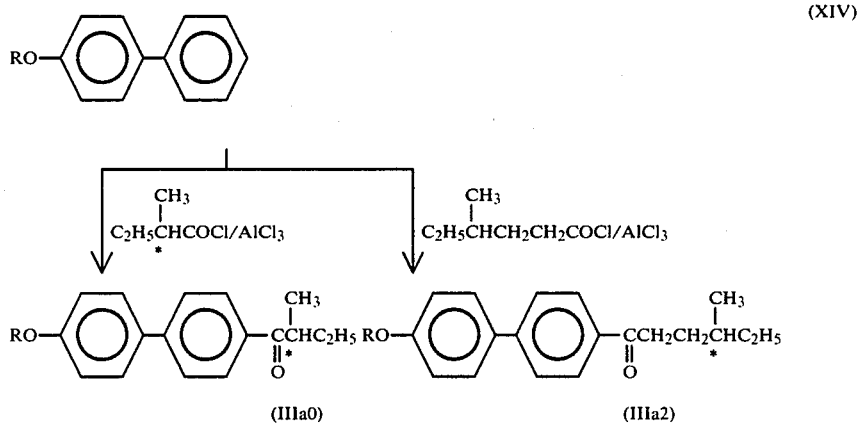

Namely, a commercially available product, p-hydroxybiphenyl (XVIII) is heated together with an alkylbromide and sodium hydroxide in a solvent to obtain a compound (XIX), which is then subjected to Friedel-Krafts reaction with 2-methylbutyric acid chloride (prepared by oxidizing (−)-2-methyl-1-butanol with potassium permanganate to obtain 2-methylbutyric acid, which is reacted with thionyl chloride) in the presence of anhydrous aluminum chloride in a solvent to obtain a compound of (IIIa0). According to this process, compounds of (IIIa0) wherein R=from methyl to octadecyl, i.e. from 4-methyloxy-4'-((S)-2-methyl-butanoyl)biphenyl to 4-octadecyloxy-4'-((S)-2-methyl-butanoyl)biphenyl are prepared.

Further, (+)-4-methyl-hexanoic acid (prepared according to K. Vogler et al, Helv. Chim. Acta, 43,279 (1960)) is reacted with thionyl chloride or the like to obtain an acid chloride (XIX), which is subjected to Friedel-Krafts reaction in the presence of anhydrous aluminum chloride in a solvent to obtain a compound of (IIIa2). According to this process, compounds of (IIIa2) wherein R=from methyl to octadecyl, i.e. from 4-methyloxy-4'-((S)-4-methyl-hexanoyl)biphenyl to 4-octadecyloxy-4'-((S)-4-methyl-hexanoyl)biphenyl, are prepared.

Next, compounds of the formula (III) wherein X=—CH₂— and n=1 (hereinafter abbreviated to (IIIb1)) are intermediate compounds previously referred to in the preparation of compounds of (IIa). According to this process, compounds of (IIIb1) wherein R=from methyl to octadecyl, i.e. from 4-methyloxy-4'-((S)-3-methylpentyl)biphenyl to 4-octadecyloxy-4'-((S)-3-methylpentyl)biphenyl are obtained.

Next, compounds of the formula (III) wherein X=CH₂ and n=2 (hereinafter abbreviated to (IIIb2)) can be prepared according to the following steps:

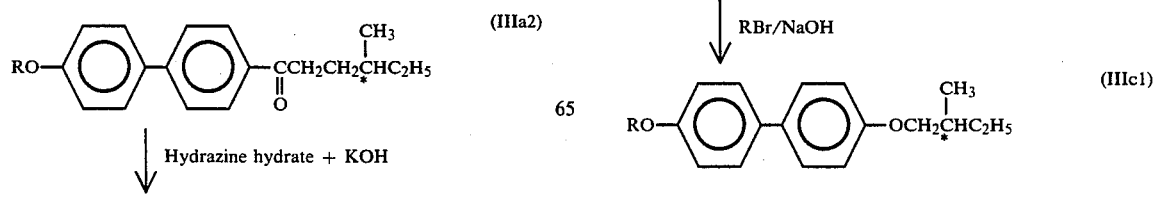

Namely, the foregoing compounds of (IIIa2) are subjected to Wolff-Kishner reduction with hydrazine and potassium hydroxide in the same manner as in the case of compounds of formula (VI), etc. to obtain compounds of (IIIb2). According to this process, compounds (IIIb2) wherein R=from methyl to octadecyl, i.e. from 4-methyloxy-4'-((S)-4-methyl-hexyl)biphenyl to 4-octadecyloxy-4'-((S)-4-methyl-hexyl)biphenyl are prepared.

Next, compounds of the formula (III) wherein X=CH₂ and n=0 (hereinafter abbreviated to (IIIb0) are obtained by etherizing compounds of (XII) described in Chart 2. According to this process, compounds of (IIIb0) wherein R=from methyl to octadecyl, i.e. from 4-methyloxy-4'-((S)-2-methyl-butyl)-biphenyl to 4-octadecyloxy-4'-((S)-2-methyl-butyl)-biphenyl are obtained. Next, compounds of the formula (III) wherein X=0 (oxygen) and n=1 (hereinafter abbreviated to (IIIc1) can be prepared according to the following steps:

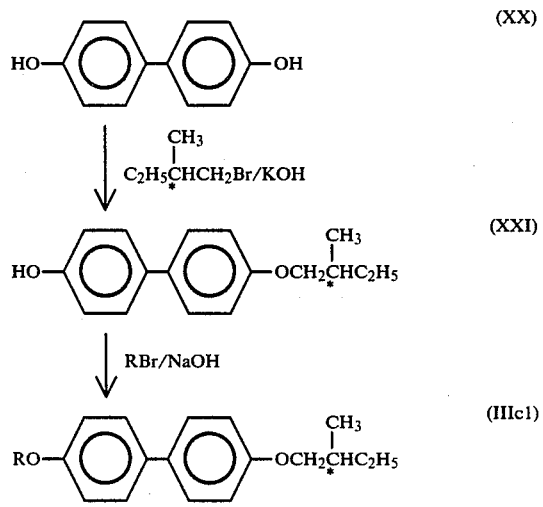

Namely, a commercially available product, p,p'-biphenol, is heated together with 2-methylbutylbromide and potassium hydroxide in a solvent to obtain a compound of (XXI), which is heated together with an alkylbromide and potassium hydroxide to obtain the objective compounds of (IIIc1). According to this process, compounds of (IIIc1) wherein R=from methyl to octadecyl, i.e. from 4-methyloxy-4'-((S)-2-methylbutyloxy)-biphenyl to 4-octadecyloxy-4'-((S)-2-methylbutyloxy)-biphenyl are obtained.

Liquid crystalline compounds and liquid crystalline compositions of the present invention will be described in more detail by way of Examples.

EXAMPLE 1

(including Examples 23 and 24)

Preparation of 4-p-octyloxybenzoyloxy-4'-(3-methyl-pentyl)biphenyl (a compound of the formula (II) wherein l=1, m=1, n=1 and R=$C_8H_{17}$)

First step

Preparation of 4-octyloxy-4'-((S)-3-methylpentanoyl)-biphenyl (a compound of the formula (III) wherein X=CO and n=1, i.e. a compound of the formula (IIIa1) wherein R=$C_8H_{17}$) Sliced Mg (12.4 g, 0.510 mol) and dry ether (50 ml) were placed in a three-neck flask in a dry nitrogen atmosphere and agitated, and to the mixture was dropwise added a solution obtained by dissolving (+)-2-methylbutyl bromide (prepared from (−)-2-methyl-1-butanol and phosphorus bromide) in dry ether (1 l), so as to keep the temperature of the system at 25° C. or lower. After completion of the dropwise addition, the mixture was allowed to stand at room temperature for 30 minutes, followed by dropwise adding a solution obtained by dissolving a commercially available product, 4-octyloxy-4'-cyanobiphenyl (IV) (129 g, 0.42 mol) in dry ether (1 l) so as to keep the temperature of the system at 10° C. or lower, thereafter refluxing for 4 hours, cooling pouring the reaction liquid in water (600 ml), further adding diluted sulfuric acid (conc. sulfuric acid 40 ml+water 80 ml), adding toluene (500 ml), transferring the mixture into a separating funnel, water-washing till the washing liquid became neutral, distilling off the solvent, distilling the residue under reduced pressure, collecting a fraction of bp 245°–255° C./4 mmHg and recrystalling from acetone (30 ml) to obtain 4-octyloxy-4'-((S)-3-methylpentanoyl)biphenyl (IIIa1) (24.6 g), which was a smectic liquid crystal exhibiting SC* phase and SA phase, and its phase transition points were as follows as shown in Table 2, column of Example 23: SA-SC* point: 68.3° C., C-SA point: 70.4° C.; SA-I point: 98.3° C.

Further, the values of elemental analysis of this compound accorded well with the calculated values as follows:

|   | Observed values | Calculated values (in terms of $C_{26}H_{36}O_2$) |
|---|---|---|
| C | 82.0% | 82.05% |
| H | 9.5% | 9.54% |

Second step

Preparation of 4-octyloxy-4'-((S)-3-methyl-pentyl)-biphenyl (a compound of formula (III) wherein X=—$CH_2$— and n=1, i.e. a compound of formula (IIIb1) wherein R=$C_8H_{17}$ 4-Octyloxy-4'-((S)-3-methyl-pentanoyl)biphenyl (24.6 g, 0.065 mol) obtained in Example 23 described later, 80% hydrazine hydrate (50 ml) and diethylene glycol (85 ml) were placed in a 500 ml three-neck flask, followed by heating with stirring, keeping the mixture at 120° C. for one hour, then cooling, adding, at a stroke, a solution of potassium hydroxide (8.8 g, 0.157 mol) in water (5 ml) while keeping the temperature at 50° C., distilling off so that the temperature of the system might become 200° C., reacting at 200° C. for 4 hours, then cooling, adding water (200 ml) and toluene (50 ml), transferring the contents into a separating funnel, water-washing the organic layer till the washing liquid became neutral, distilling off the solvent, distilling under reduced pressure to collect a fraction having a boiling point of 210°–213° C./3 mmHg, and recrystallizing it from ethyl alcohol (20 ml) and ethyl acetate (5 ml) to obtain 4-octyloxy-4'-((S)-3-methyl-pentyl)biphenyl (IIIb1) (13.5 g) which was a smectic liquid crystal exhibiting SC* phase and SH* phase, and whose phase transition points were as follows as shown in Table 2, column of Example 24: C-$S_1$ point, 43.0° C.; Sl-SH* point, 57.9° C.; SH*-SC* point, 62.5° C; SC*-I point, 65.1° C.

Further, the values of elemental analysis of this compound accorded well with the calculated values as follows:

|   | Observed values | Calculated values (in terms of $C_{26}H_{38}O$) |
|---|---|---|
| C | 85.2% | 85.19% |
| H | 10.4% | 10.45% |

Third step

Compound (IIIb1) (13.5 g, 0.037 mol) obtained in the second step, acetic acid (120 ml) and 47% hydrobromic acid (15 ml) were placed in a 500 ml three-neck flask and refluxed with stirring for 40 hours, followed by cooling, adding water (150 ml) and toluene (50 ml), transferring the mixture into a separating funnel, water-washing till the washing liquid became neutral, distilling off and recrystallizing from n-heptane (10 ml) to obtain a compound (VII) (6.5 g). M.p.: 120.7°~122.6° C.

Fourth step p-Octyloxybenzoic acid chloride (0.48 g, 0.002 mol) was added to and reacted with a solution of compound (VII) (0.5 g, 0.002 mol in dry pyridine (2 ml), followed by well agitating, allowing to stand overnight, adding toluene (20 ml) and water (10 ml), washing with 6N-HCl, then with 2N NaOH solution, further water-washing till the washing liquid became neutral, distilling off toluene and recrystallizing the residue from ethanol to obtain the objective 4-p-octyloxybenzoyloxy-4'-(3-methyl-pentyl)biphenyl (0.3 g). The values of elemental analysis of this compound accorded well with the calculated values as follows:

|   | Observed values (% by weight) | Calculated values (in terms of $C_{33}H_{42}O_3$) (% by weight) |
|---|---|---|
| C | 81.35 | 81.44 |
| H | 8.5 | 8.7 |

This compound is a liquid crystalline compound exhibiting SC* phase and Ch phase and its phase transition temperatures are shown in Table 1.

EXAMPLES 2–22

Example 1 was repeated except that p-octyloxybenzoic acid chloride used in the fourth step of Example 1 was replaced by various p-alkoxybenzoic acid chlorides, p-alkylbenzoic acid chlorides, alkyl chloroformates or aliphatic acid chlorides, to prepare compounds of the formula (II) shown in Table 1. Their phase transition points are also shown in Table 1.

EXAMPLES 23–24

A compound of the formula (IIIa1) wherein $R'=C_5H_{17}$ (Example 23) is described in the first step of Example 1, and a compound of the formula (IIIb1) wherein $R'=C_8H_{17}$ (Example 24) is described in the second step of Example 1.

EXAMPLE 25

Preparation of 4-octyloxy-4'-((S)-2-methyloxy)biphenyl (a compound of the formula (III) wherein $X=O$ and $n=1$, i.e. a compound of the formula (IIIc1) wherein $R'=C_8H_{17}$)

(i) Preparation of 4-hydroxy-4'-((S)-2-methylbutyloxy)biphenyl

A mixture of 4,4'-dihydroxybiphenyl (500 g), ethyl alcohol (7.5 l) and potassium hydroxide (302 g) was heated with stirring under reflux, and (+)-2-methylbutylbromide (prepared from (−)-2-methylbutanol and phosphorus bromide) (530 g) was dropwise added to carry out reaction for 4 hours, followed by distilling off ethanol, adding water (2 l), filtering, collecting insoluble matter, adding toluene to this insoluble matter to dissolve and remove toluene-soluble matter (this soluble matter, when recrystallized from ethyl alcohol, gave scaly crystals having a m.p. of 80.5° C.; thus the compound was confirmed to be 4,4'-di((S)-2-methylbutyloxy)biphenyl), heating the insoluble matter together with 3N-hydrochloric acid with stirring, cooling solid matter and recrystallizing from toluene and then from ethyl alcohol to obtain 4-hydroxy-4'-((S)-2-methylbutyloxy)-biphenyl (XXI) having a m.p. of 137.5° C. (125 g).

(ii) Ethyl alcohol (5 ml), sodium hydroxide (4.6 g, 0.01 mol) and water (0.5 ml) were added to 4-hydroxy-4'-((S)-2-methylbutyloxy)biphenyl (2 g) obtained in the above item (i), and heated to 50° C. with stirring, followed by adding, at a stroke, octyl bromide (1.9 g, 0.01 mol), refluxing for 4 hours, cooling, adding water (10 ml) and toluene (30 ml), transferring the mixture into a separating funnel, washing the organic layer with 6N-HCl aqueous solution and then with 2N-NaOH aqueous solution, water-washing till the washing liquid became neutral, distilling off the solvent and recrystallizing the residue from ethyl alcohol to obtain the objective 4-octyloxy-4'-((S)-2-methylbutyloxy)biphenyl (IIIc1) (0.8 g), which was a smectic liquid crystal exhibiting $S_1$ phase and SH* phase and whose phase transition points are shown in Table 2.

The values of elemental analysis of this compound accorded well with the calculated values as follows:

|   | Observed values | Calculated values (in terms of $C_{25}H_{36}O_2$) |
|---|---|---|
| C | 81.4% | 81.45% |
| H | 9.8% | 9.85% |

EXAMPLES 26–33

Compounds of the formula (III) having other alkyl groups were prepared in the same manner as in Example 23, 24 or 25. Their phase transition points are shown in Table 2 together with the results of Examples 23–25.

EXAMPLE 34

(Use example 1)

A nematic composition consisting of

| | |
|---|---|
| 4-ethyl-4'-cyanobiphenyl | 20 parts weight |
| 4-pentyl-4'-cyanobiphenyl | 40 parts weight |
| 4-octyloxy-4'-cyanobiphenyl | 25 parts weight and |
| 4-pentyl-4'-cyanoterphenyl | 15 parts weight | was filled in a TN display cell of transparent electrodes (the distance therebetween: 10 μm) subjected to parallel aligning treatment by applying PVA and rubbing the surfaces, and when it was observed with a polarizing microscope, a reverse domain was observed.

To the above nematic liquid crystalline composition was added 0.1% by weight of a compound of the present invention recited in the column of Example 9 in Table 1 (a compound of the formula (II) wherein $l=1$, $m=1$, $n=1$ and $R=C_3H_7$), and using the resulting composition, a TN cell was similarly prepared. As a result of observing the cell, the reverse domain disappeared and a uniform nematic phase was observed.

EXAMPLE 35

(Use example 2)

A mixture in equal amounts of 5 compounds of Examples 5, 7, 15, 16 and 17 exhibited SC* phase up to 109° C. and exhibited a cholesteric phase at higher temperatures than the above to form an isotropic liquid at 135° C.

This mixture was poured in a cell equipped with transparent electrodes subjected to parallel aligning treatment by applying PVA and rubbing the surfaces, and slowly cooled as far as SC* phase was attained, while a direct current voltage of 50 V was impressed thereto within Ch phase region. As a result, a uniform monodomain cell was obtained.

The resulting cell was placed between two pieces of polarizers arranged so as to give a perpendicularly crossed Nicol state, and when an alternate current of 15 V and low frequency (0.5 Hz) was impressed, a clear switching effect was observed and a liquid crystal display element having a very good contrast and a high response rate (2 m sec.) was obtained.

In addition, the value of spontaneous polarization, Ps of this composition was 1 n $C/cm^2$.

EXAMPLE 36

(Use example 3)

A liquid crystal mixture of a compound expressed by

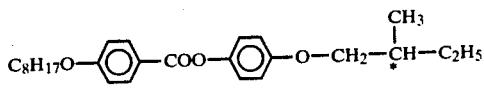

(80% by weight) and compounds of Examples 7 and 14 in Table 1 (each 10% by weight) exhibited SC* phase up to 47° C. and exhibited SA phase at higher temperatures than the above to form Ch phase at 64° C. and form an isotropic liquid at 72° C.

To this mixture was added 3% by weight of an anthraquinone dyestuff D-16 (a product of BDH company) to form a material of the so-called guest-host type. It was poured in the same cell as in Example 34, and one piece of polarizer was arranged so that the polarization surface might be perpendicular to the axis of molecular axis. When an alternate current of 15 V and low frequency (0.5 Hz) was impressed, a clear switching effect was observed and a color liquid crystalline display element having a very good contrast and a high response rate (2 m sec) was obtained.

In addition, the value of spontaneous polarization, Ps of this composition was 2 n C/cm$^2$.

EXAMPLE 37

(Use example 4)

A composition consisting of

| | |
|---|---|
| 4-ethyl-4'-cyanobiphenyl | 20 parts weight |
| 4-pentyl-4'-cyanobiphenyl | 40 parts weight |
| 4-octyloxy-4'-cyanobiphenyl | 25 parts weight and |
| 4-pentyl-4'-cyanoterphenyl | 15 parts weight | was filled in a TN cell of transparent electrodes (the distance therebetween: about 10 μm) subjected to parallel aligning treatment by applying PVA and rubbing the surfaces, and when it was observed with a polarizing microscope, a reverse domain was observed.

To the above nematic liquid crystalline composition was added 1% by weight of a compound of the present invention of Example 26 (a compound of the formula (III) wherein X=—O—, n=1, and R=C$_6$H$_{13}$), and using the resulting composition, a TN cell was similarly prepared. As a result of observing the cell, the reverse domain disappeared and a uniform nematic phase was observed.

EXAMPLE 38

(Use example 5)

A mixture consisting of compounds of Examples 25, 27 and 28 (each 10% by weight), compounds of Examples 24 and 32 (each 20% by weight) and a compound of Example 33 (30% by weight) exhibited SH* phase up to 64° C., exhibited SC* phase up to 66° C., and exhibited SA phase at higher temperatures than the above to form an isotropic liquid at 70° C.

This mixture was poured in a cell equipped with transparent electrodes subjected to parallel aligning treatment by applying PVA and rubbing the surfaces, and slowly cooled as far as SC* phase was attained, while a direct current voltage of 50 V was impressed thereto. As a result, a uniform monodomain cell was obtained.

The resulting cell was placed between two pieces of polarizers arranged so as to give a perpendicularly crossed Nicol state, and when an alternate current of 15 V and low frequency (0.5 Hz) was impressed, a clear switching effect was observed and a liquid crystal display element having a very good contrast and a high response rate (2 m sec.) was obtained.

In addition, the value of spontaneous polarization, Ps of this composition was 2 n C/cm$^2$.

EXAMPLE 39

(Use example 6)

A mixture consisting of compounds of Examples 27 and 28 (each 10% by weight) and compounds of Examples 23, 24, 32 and 33 (each 20% by weight) exhibited SH* phase up to 57° C., exhibited SC* phase up to 60° C. and exhibited SA phase at higher temperatures than the above to form an isotropic phase at 67° C.

To this mixture was added 3% by weight of an anthraquinone dyestuff D-16 (a product of BDH company) to form a material of the so-called guest-host type. It was poured in the same cell as in Example 38, and one piece of polarizer was arranged so that the polarization surface might be perpendicular to the axis of molecular axis. When an alternate current of 15 V and low frequency (0.5 Hz) was impressed, a clear switching effect was observed and a color liquid crystalline display element having a very good contrast and a high response rate (2 m sec) was obtained.

In addition, the value of spontaneous polarization, Ps of this composition was 1 n C/cm$^2$.

What we claim is:

1. Liquid crystalline compounds expressed by the formula

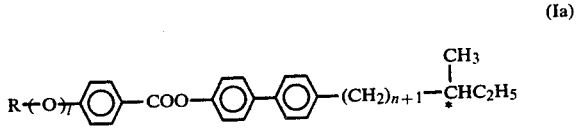

(Ia)

wherein
l is 0 or 1, and
n is 1,
R represents an alkyl group having 5 to 10 carbon atoms when l is 0 and 4 to 13 carbon atoms when l is 1,
* indicates an optically active carbon compound.

2. A compound according to claim 1 wherein l is 0.
3. A compound according to claim 1 wherein l is 1.
4. A chiral smectic liquid crystalline composition comprising at least two components, one of which is a compound having the formula set forth in claim 1.
5. A chiral smectic liquid crystalline composition comprising at least two components, one of which is a compound having the formula set forth in claim 2.
6. A chiral smectic liquid crystalline composition comprising at least two components, one of which is a compound having the formula set forth in claim 3.

* * * * *